United States Patent [19]

Virgilio et al.

[11] 4,216,342

[45] Aug. 5, 1980

[54] PROCESS FOR THE PURIFICATION OF CRUDE 2,4,5-TRICHLOROPHENOL

[75] Inventors: Joseph A. Virgilio, Wayne; Joachim E. Freudewald, Morristown, both of N.J.

[73] Assignee: Givaudan Corporation, Clifton, N.J.

[21] Appl. No.: 25,419

[22] Filed: Mar. 30, 1979

[51] Int. Cl.$^2$ .............................................. C07C 39/24
[52] U.S. Cl. ...................................... 568/755; 568/776
[58] Field of Search ................ 568/755, 725, 776, 727

[56] References Cited

U.S. PATENT DOCUMENTS

| | | | |
|---|---|---|---|
| 3,426,081 | 2/1969 | Shore et al. | 568/725 |
| 3,499,045 | 3/1970 | Cleary | 568/755 |
| 3,707,568 | 12/1972 | Michael | 568/755 |

*Primary Examiner*—Werren B. Lone
*Attorney, Agent, or Firm*—Robert F. Tavares; Thomas Cifelli, Jr.

[57] ABSTRACT

A novel process for the purification of 2,4,5-trichlorophenol which comprises selectively reacting the major impurities with formaldehyde.

11 Claims, No Drawings

PROCESS FOR THE PURIFICATION OF CRUDE 2,4,5-TRICHLOROPHENOL

BACKGROUND OF THE INVENTION

The conventional industrial method for preparing 2,4,5-trichlorophenol involves the reaction of 1,2,4,5-tetrachlorobenzene with methyl alcoholic or aqueous methyl alcoholic sodium hydroxide. The crude product which is available commercially is about 94% 2,4,5-trichlorophenol and about six percent impurities which are primarily dichlorophenols and dichloromethoxyphenols.

The germacide known as Hexachlorophene® (bis-[3,5,6-trichloro-2-hydroxyphenyl]methane), is prepared by condensing 2,4,5-trichlorophenol with formaldehyde. In order to get a germicide of high purity, it is desirable to start with a 2,4,5-trichlorophenol of high purity. Since the dichlorophenols and dichloromethoxyphenols present in the commercial grade 2,4,5-trichlorophenol will also react with formaldehyde, it is desirable to remove them prior to the condensation.

SUMMARY OF THE INVENTION

It is the surprising and unexpected finding of this invention that major impurities in the crude product (ca. 94% 2,4,5-trichlorophenol and ca. 5.5% dichlorophenols+dichloromethoxyphenols) can be reacted with formaldehyde under conditions wherein the undesired 5.5% of the impurities react to form condensation products, but the 2,4,5-trichlorophenol does not react to form Hexachlorophene. The unreacted 2,4,5-trichlorophenol can then be separated from the condensation products to provide 99.5% pure 2,4,5-trichlorophenol in high yield.

The critical parameters in this process appear to be the concentration of sulfuric acid, the reaction temperature and the time the reaction is allowed to run.

DESCRIPTION OF THE PREFERRED EMBODIMENTS

The method disclosed herein depends upon the ability to judiciously choose reaction conditions wherein the undesirable impurities will form condensation products with the formaldehyde while the 2,4,5-trichlorophenol will not.

The form of the formaldehyde is not critical. Formaldehyde added as a 37% aqueous solution or formaldehyde added as paraformaldehyde are both suitable.

The nature or amount of excess of the formaldehyde used does not appear to be critical. Although stoichiometry demands only one mole of formaldehyde for every two moles of phenolic impurity to be condensed, it is preferred to add an excess of several fold since the reagent is economical and an excess does not have a detrimental effect on the purification process.

An amount of formaldehyde greater than 1 mole per mole of impurity to be removed would be suitable with an amount of 2 to 5 moles/mole preferred. About 3 moles per mole is especially preferred.

The concentration of the sulfuric acid appears to be the most critical factor. When the sulfuric acid concentration is 50% or less, the yields of recovered 2,4,5-trichlorophenol were lower and the improvement in the purity was only marginal. When the concentration of sulfuric acid is 80% or greater, the 2,4,5-trichlorophenol reacts rapidly with the formaldehyde and the result is a lower recovery of 2,4,5-trichlorophenol and only a marginal, if any, improvement as to the purity of the recovered material.

By contrast, at sulfuric acid concentrations between 55% and 75% there is a surprising selectivity demonstrated with the formaldehyde reaction primarily with the dichlorophenol and methoxydichlorophenol impurities and not with the 2,4,5-trichlorophenol. It is preferred to work at the center of this range of concentrations, i.e. at concentrations of 60% to 70%.

The temperature range is less critical than the acid concentration, but should be carefully controlled to insure maximum recovery of high quality 2,4,5-trichlorophenol. Temperatures below 70° C. result in a sluggish reaction between the impurities to be removed and the formaldehyde resulting in a poorer grade of recovered 2,4,5-trichlorophenol.

At temperatures exceeding 90° C. the reaction appears to be less selective and lower yields of recovered 2,4,5-trichlorophenol are obtained. Temperatures in the range of 70° C. to 90° C. are, therefore, preferred. It is especially preferred to work in the middle of this range at temperatures of from 75° C. to 85° C.

The reaction should, of course, be run until all of the impurities to be removed have condensed with the formaldehyde. Under the preferred conditions, this normally occurs from five to eight hours. It is preferred however, to follow the reaction by a suitable analytical tool such as gas liquid chromatography.

The purified 2,4,5-trichlorophenol can be separated from the heavier condensation products by methods known in the art, i.e. by extraction and/or distillation.

A number of suitable extraction solvents will dissolve the trichlorophenol, but not the less soluble bis-phenols. Suitable for this purpose are the alkane solvents such as pentane, hexane, heptane and the like.

It is preferred to separate the lower boiling trichlorophenol from the higher boiling condensation products by a distillation, preferably a steam distillation or vacuum steam distillation.

ILLUSTRATION OF THE PREFERRED EMBODIMENTS

A number of examples are provided herein to illustrate the preferred embodiments of this invention. They are included for the purpose of illustration only and should not be construed as limiting. They are intended to embrace any equivalents or obvious extensions which are known or should be known to a person skilled in the art.

The purity of the 2,4,5-trichlorophenol was determined by vapor phase chromatography using a ⅛ in. ×6 ft. stainless steel column packed with 4% FFAP on 100/120 mesh chromsorb W, acid washed, DMCS. A flame ionization detector was used.

The commercial technical grade 2,4,5-trichlorophenol that was purified in these examples was purchased from vendors who are in the business of manufacturing and selling this material and was analysed by gas liquid chromatography as follows:

| | |
|---|---|
| 2,4,5-Trichlorophenol | 94.0 ± 0.2% |
| 2,4/2,5-Dichlorophenol | 1.0 ± 0.8% |
| 2,3,6/2,4,6-Trichlorophenol | 0.3 ± 0.3% |
| 3,4-Dichlorophenol | 0.1 ± 0.1% |
| 4,5-Dichloro-2-methoxyphenol } | |
| 2,5-Dichloro-4-methoxyphenol | 4.6 ± 0.7% |

| | |
|---|---|
| -continued | |
| 2,4-Dichloro-5-methoxyphenol | |

The term technical grade TCP refers to a commercially available product similar to that described above and which is about 94% 2,4,5-trichlorophenol. This term (technical grade TCP) when used hereinafter refers to such a commercially available product.

EXAMPLE I

Sulfuric acid (903 grams of 93% $H_2SO_4$) was diluted by slowly adding it to cold water (347 g) which was cooled and stirred during the addition. Technical grade TCP was added and the reaction mixture heated to and subsequently maintained at 80° C.

Aqueous formaldehyde (14.0 g of a 37% solution) was added slowly over a period of four hours. The reaction mixture was maintained at 80° C. for an additional two hours.

The reaction mixture was diluted by adding about 600 ml water and the product isolated via a steam distillation.

There was obtained 206.5 g of 2,4,5-trichlorophenol which was 99.5% pure. This represents an 87.7% recovery of the 2,4,5-trichlorophenol in the starting material.

The purified product analysed as follows:

| | |
|---|---|
| 2,4,5-Trichlorophenol | 99.5 |
| 2,4/2,5-Dichlorophenol | — |
| 2,3,6/2,4,6-Trichlorophenol | 0.3 |
| 3,4-Dichlorophenol | — |
| 4,5-Dichloro-2-methoxyphenol | |
| 2,5-Dichloro-4-methoxyphenol | 0.2 |
| 2,4-Dichloro-5-methoxyphenol | |

EXAMPLE II

Example I was repeated, substituting 5 g of paraformaldehyde for the 14 g of 37% aqueous formaldehyde. The paraformaldehyde was added portionwise over a 30 minute period.

Pure 2,4,5-trichlorophenol (200.9 g, 85.5% yield, 99.6% pure) was recovered.

EXAMPLE III

Example I was repeated excepting that 21 g of aqueous formaldehyde was used.

Pure 2,4,5-trichlorophenol (200.9 g, 85.5% yield, 99.7% pure) was recovered.

EXAMPLE IV

The process of Example II was repeated using a hot heptane extraction in place of the steam distillation.

There was 190.6 g of 2,4,5-trichlorophenol recovered (91.1% yield, 98.3% pure).

EXAMPLE V

Example I was repeated excepting that a temperature of 100° C. was used. There was 167.1 g of 2,4,5-trichlorophenol recovered (71.0% yield, 99.6% pure). This is considerably less than obtained in Example I illustrating the fact that temperatures in excess of 90° C. result in lower recovery of the desired product.

EXAMPLE VI

Example II was repeated excepting that a sulfuric acid concentration of 50% was used. Product recovered was only 96.2% pure. This illustrates the poor results obtained at low acid concentrations.

EXAMPLE VII

Example I was repeated and followed by gas liquid chromatography to illustrate the shorter reaction times result in a product of lower purity.

After 1 hr 94.7% pure 2,4,5-trichlorophenol recoverable.

After 2 hrs 95.1% pure 2,4,5-trichlorophenol recoverable.

After 4 hrs 98.7% pure 2,4,5-trichlorophenol recoverable.

After 6 hrs. 99.5% pure 2,4,5-trichlorophenol recoverable.

EXAMPLE VIII

Example I was repeated and the 2,4,5-trichlorophenol was recovered via a vacuum steam distillation.

There was recovered 208.0 g (88.5% yield, 99.3% pure).

EXAMPLE IX

Example I was repeated excepting that the concentration of the sulfuric acid used was 80%. The 2,4,5-trichlorophenol reacted with the formaldehyde to form a bis-phenol. This example illustrates the failure of the purification process if the concentration of acid gets too high.

We claim:

1. Process for the purification of technical grade TCP which comprises treating the technical grade TCP with formaldehyde in the presence of 55% to 75% sulfuric acid at a temperature between 70° C. and 90° C. and separating purified TCP therefrom.

2. A process according to claim 1 wherein the purified TCP is isolated by a distillation or an extraction.

3. A process according to claim 2 wherein the purified TCP is isolated by a steam distillation or a vacuum steam distillation.

4. A process according to claim 1 wherein 60-70% sulfuric acid is used.

5. A process according to claim 4 wherein the temperature is between 75° C. and 85° C.

6. A process according to claim 5 wherein the product is isolated by a distillation or an extraction.

7. A process according to claim 6 wherein the product is isolated by a distillation.

8. A process according to claim 1 wherein there is used:
   (a) two to five molar equivalents of formaldehyde
   (b) 60% to 70% sulfuric acid;
   (c) a reaction temperature of 75° C. to 85° C.;
   (d) a steam distillation or vacuum steam distillation for the isolation of the purified 2,4,5-trichlorophenol.

9. The process of claim 8 wherein the reaction time is 5 to 8 hours.

10. The process of claim 9 wherein aqueous formaldehyde is used.

11. The process of claim 9 wherein paraformaldehyde is used.

* * * * *